United States Patent [19]

Sutherland

[11] Patent Number: 4,638,059
[45] Date of Patent: Jan. 20, 1987

[54] GEL-FORMING POLYSACCHARIDES

[75] Inventor: Ian W. Sutherland, Edinburgh, Scotland

[73] Assignee: National Research Development Corp., London, England

[21] Appl. No.: 625,548

[22] Filed: Jun. 28, 1984

[30] Foreign Application Priority Data

Jul. 7, 1983 [GB] United Kingdom ............... 8318403

[51] Int. Cl.⁴ .............................................. C08B 37/00
[52] U.S. Cl. .................................... 536/121; 536/1.1; 536/123
[58] Field of Search ................. 536/1.1, 114, 123, 121

[56] References Cited

U.S. PATENT DOCUMENTS

| | | | |
|---|---|---|---|
| 3,335,127 | 8/1967 | Polson | 536/114 |
| 4,057,509 | 11/1977 | Costanza et al. | 536/114 |
| 4,112,220 | 9/1978 | Carroll et al. | 536/114 |
| 4,186,025 | 1/1980 | Kang et al. | 536/114 |
| 4,329,448 | 5/1982 | Cox et al. | 536/114 |

OTHER PUBLICATIONS

Chemical Abstracts 80, 131678b (1974) (Ajinomoto).
Patents Abstracts of Japan 3, No. 50 (C-44) (1979) (Kuraray).
Chemical Abstracts 98, 33072h (1983) (Nichiden).
B. A. Nisbet, I. W. Sutherland, I. J. Bradshaw, Margaret Kerr,: XM6-A New Gel-Forming Polysaccharide from Bacteria, Dept. of Microbiology, Univ. of Edinburgh, Edinburgh, Scotland.

*Primary Examiner*—Johnnie R. Brown
*Attorney, Agent, or Firm*—Murray and Whisenhunt

[57] ABSTRACT

The invention provides a polysaccharide which undergoes cation-induced gelation to form gels of useful strength at relatively low concentration of cation, and which melt and set sharply and reversibly. It has a marked preference in terms of gel strength for cations of sodium rather than other Group Ia elements and calcium rather than other Group IIa elements. It contains D-glucose, L-fucose and D-glucuronate residues in the approximate molar ratio of 3:1:1. The polysaccharide can be isolated from the bacterium NCIB 11870. Its gels are useful in food and medicine for addition to a variety of foodstuffs and pharmaceuticals. They can be prepared simply by adding the appropriate cations to a dilute aqueous solution of the polymer at ambient temperature, whereupon the gel forms rapidly. If desired the gel initially formed can be melted and re-set.

7 Claims, 7 Drawing Figures

GEL-FORMING POLYSACCHARIDES

This invention relates to gel-forming polysaccharides.

Although an increasing number of microbial polysaccharides have been examined for potentially useful physical properties, relatively few appear to be capable of gel formation. One exception is curdlan, a 1,3-linked beta-D-glucan synthesised by Agrobacterium spp. and by *Rhizobium meliloti*, T. Harada in "Polysaccharides in Food", eds. J. M. V. Blanshard and J. M. Mitchell, Butterworths, London, p. 283 (1979); and T. Harada and A. Amemura, Mem. Inst. Sci. Ind. Res. Osaka Univ. 38, 37, (1981). Another gel-forming polymer is an acetylated heteropolysaccharide from *Pseudomonas elodes* containing glucose, rhamnose and uronic acid in the approximate ratio 2:3:1, I. W. Cottrell, American Chemical Society Symposium series 126 252, (1980); R. Moorhouse et al., ib id, 150, 111 (1981); and K. S. Kang et al., Appln. env. Microbiol. 43, 1086 (1982). This material was unusual in that aqueous solutions, after heating and cooling, formed a weak and very elastic gel. Following deacetylation at pH 10.0, the polysaccharide forms firm non-elastic brittle gels with a melting point of 90° C.

A microbial polysaccharide has now been isolated as an extracellular product of a Gram-negative bacterium and has unusual and potentially valuable gelation behaviour. The newly isolated polysaccharide shows unusual gelation properties of potential technological significance. It contains D-glucose, L-fucose and D-glucuronate residues in the approximate molar ratio 3:1:1. No significant amounts of acetate or pyruvate were detected. D-Glucuronate and some D-glucose are destroyed on periodate oxidation, but L fucose and some D-glucose can be recovered intact, indicating the presence of some 1,3-linkages in the primary structure. The major oligosaccharide isolated from auto-hydrolysates was an aldobiuronic acid containing equal amounts of D-glucuronic acid and L-fucose.

Thermally-reversible gels, i.e. which melt and set reversibly, are formed on addition of salts to solutions of the polysaccharide. Divalent cations are in general more effective than monovalent in promoting gelation of the polysaccharide, while trivalent cations normally cause precipitation. Among cations of Groups Ia and IIa of the Periodic Table, optimum gel strength is achieved with $Na^+$ and $Ca^+$ (ionic radius about 0.1 nm), larger and smaller ions becoming progressively less effective. Both gel strength and melting temperature increase with increasing salt concentration.

The polysaccharide forms gels of reasonable strength at concentrations of the polysaccharide, which are unusually low, matched only by the expensive polysaccharide agar. For example, gels comparable to those required for normal industrial or food applications may be obtained using a 0.3% w/v aqueous solution of the polysaccharide and 1% w/v sodium chloride solution (about 0.2 M). Gel strength increases with increasing polymer concentration but there is no systematic variation in melting point with polymer concentration. The gel-sol, i.e. the melting, transition of the polysaccharide is unusually sharp and, by suitable adjustment of salt concentration, can be made to occur just below body temperature (e.g. 30°-35°), and the gel is therefore useful in biomedical or food applications. An example of a biomedical use is as the vehicle for a gel, cream or lotion.

Two well known gelling polysaccharides are the glycuronans, pectic and alginic acid. They are comrposed solely of hexuronic acid residues; alginic acid contains D mannuronic acid and L-guluronic acid and all linkages are 1,4; pectic acid contains D-galacturonic acid. Other gelling compositions are agar and carrageenan. Agar contains D-galactose and 3,6-anhydro-L-galactose, with pyruvate ketals and sulphate esters. Carrageenan contains 4 O-substituted D-galactose-2,6 disulphate residues. No microbial polysaccharides containing sulphate have yet been described. Both agar and carrageenan are mixtures of molecular species.

The newly isolated polysaccharide has in common with alginate and pectate that it forms cation-associated gels, but differs from alginate and pectate in that a gel of reasonably high strength can be formed at a lower concentration of the cation. The newly isolated polysaccharide has in common with carrageenan and agar that its cation-associated gels melt rapidly. It differs from them in that it has a preference (in terms of gel strength) for cations of a particular ionic radius (sodium and calcium) over other ions (of smaller and larger radius) of the same groups (Ia and IIa) of the Periodic Table.

The present invention comprises the newly isolated polysaccharide and any similar polysaccharides, e.g. which might be obtainable from closely related bacteria, presenting a generally similar distinction over known polysaccharides. Various combinations of some of the chemical and/or physical properties described herein are capable of defining these polysaccharides. According to one important definition of the polysaccharides of the invention:

(1) they contain D-glucose, L-fucose and D-glucuronate residues in the approximate molar ratio of 3:1:1;

(2) when oxidised by periodate they give a product containing some only of the D glucose residues of the unoxidised polymer, substantially all the L-fucose residues of the unoxidised polymer and substantially no D-glucuronate;

(3) they form gels when cations of at least any one of the elements lithium, sodium, potassium, rubidium and caesium of Group Ia of the Periodic Table and magnesium, calcium, strontium and barium of Group IIa of the Periodic Table are added to an aqueous solution of the polymer;

(4) the gels thus formed melt on heating and set on cooling reversibly;

(5) the strength of the gels increases with increasing concentration of the polymer in aqueous solution;

(6) the polymers form stronger gels with Group Ia and IIa cations of a particular ionic radius than with other Group Ia and IIa cations; and (7) they are obtainable by isolation from the bacterium NCIB 11870 as defined hereinafter, or a variant or mutant thereof.

Optionally the polysaccharide can be further characterised in that the gel formed by addition of 0.17 M aqueous sodium chloride solution to a 0.3% w/v (g/100 ml) aqueous solution of the polymer at ambient temperature has a yield stress at 25° C. of the order of at least 10 g.cm.$^{-2}$.

The newly isolated polysaccharide of the invention is obtainable by culturing the bacterium NCIB 11870, which has been deposited as a patent deposit at the National Collection of Industrial Bacteria, c/o The National Collections of Marine and Industrial Bacteria Ltd., Torry Research Station, P O Box 31, 135 Abbey Road, Aberdeen, Scotland AB9 8DG on 10 June 1983 under the above Accession Number. The bacterial strain was isolated in the laboratory from a carbohydrate-rich environment. It is Gram-negative and takes the form of rods, approximately 2-3 micrometers×1 micrometer. It is non-motile. It grows well in nutrient broth, Davis/Mingioli and other relatively simple media, growth being assisted by the presence of small quantities of yeast extract of casein hydrolysate. It forms colonies after about six days on Davis/Mingioli or similar media. The colonies are of diameter 4-5 mm, grey-white translucent, circular, convex and extremely viscous leading to trails of polymer from a needle inserted into such colonies. Growth is optimum at or near 35° C., poor at temperatures above 39° C. or below 10° C. The bacterium is a facultative anaerobe, but is best grown aerobically. Results of standard tests are: oxidase negative; methyl red negative; Voges-Proskauer positive; citrate utilised; fermentation of D glucose, D-fructose, D-mannose, D-xylose, D-galactose, D-mannitol, sucrose and trehalose, in all cases with production of acid and gas; starch hydrolysis negative. It produces the polysaccharide of the invention on media containing an acceptable carbon source, for example glucose or sucrose, D-Fructose, D-mannose, or glutamic acid could be used but is less preferred. The bacterial strain has been tentatively assigned to the Enterobacter species.

The invention includes the bacterium NCIB 11870 as defined by the deposit details given above, variants and mutants thereof. It also includes a biologically pure culture thereof. It includes a method of preparing the newly isolated polysaccharide of the invention which comprises culturing NCIB 11870 at a temperature from 10° to 39° C. with a source of assimilible carbon and separating the polysaccharide thereby produced extracellularly.

Although the newly isolated polysaccharide of the invention is defined inter alia as obtainable from NCIB 11870, it must be emphasised that such definition is not intended to limit the polysaccharide to one actually obtained from such a bacterium (and still less from the particular sample thereof deposited at the NCIB). In other words, the "obtainable by . . . " element of the definition is included merely because of the difficulty of formulating a full chemical definition and to aid in identifying the polysaccharide. Thus the same polysaccharide (or, as explained above, any similar one) produced partially or wholly by chemical synthesis or by recombinant DNA technology or by bacterial synthesis from a different culture, strain, species, or even genus of microorganism is not excluded from the ambit of the present invention.

Besides the polysaccharides themselves the invention includes a gellable aqueous composition (which may be a solution or a sol) containing a polysaccharide of the invention and a gel-forming cation, which is normally of Group Ia (lithium to rubidium) or IIa (beryllium or barium) of the Periodic Table, although other cations are not excluded. Ammonium ($NH_4^+$) is an example of such another cation. Sodium and calcium are preferred for gelling the newly isolated polysaccharide, i.e. the specific embodiment product of the invention. Any anion can be supplied e.g. chloride or hydroxide. The gel and the process of gelation by setting the gellable composition, preferably by allowing it to set at ambient temperature, or if necessary upon heating or cooling, are also part of the present invention.

The resulting gels are thermally reversible and show sharp melting and setting behaviour. More homogeneous and cohesive gels may be obtained by melting the gel formed initially at room temperature and allowing it to reform on cooling, or by mixing polymer and salt solutions at a temperature above the melting point of the final gel.

The ionic concentration required varies widely for different salts and, in common with other gelling polymers, a minimum critical concentration of the polysaccharide is required for gel formation. In general, gels of comparable strength to those normally used for typical industrial or food applications may be obtained at a polymer concentration of about 0.3%, i.e. somewhat higher than for agar, but appreciably lower than for carrageenan, alginate, gelatin or starch.

Hereinafter the invention is described and illustrated by reference to the newly isolated polysaccharide which for convenience is called simply the "polysaccharide" or the "polymer". Concentrations of polysaccharide in w/v are metric, i.e. g/ml. All other percentages are by weight unless the context implies otherwise.

The following Table shows properties of gels of the invention obtained by adding various salts as shown to aqueous solutions of the polysaccharide, as shown. Divalent cations are in general more effective than monovalent in the gelation, while trivalent cations normally cause the polymer to precipitate. Cohesive gels were, however, obtained with $Fe^{3+}$ ions over the concentration range 0.30–0.34 mM.

TABLE

| | Properties of gel of the invention | | | |
|---|---|---|---|---|
| Polymer % w/v | Salt | Salt conc. (mM) | Melting temperature (°C.) | Gel strength (g · cm.$^{-2}$) |
| 0.1 | NaCl | 170 | 30 | — |
| 0.1 | | 509 | 40 | 1.3 |
| 0.2 | | 170 | 33 | 2.8 |
| 0.2 | | 509 | 45 | 7.7 |
| 0.3 | | 170 | 30 | 11.3 |
| 0.3 | | 509 | 45 | 15.1 |
| 0.1 | KCl | 133 | 33 | 1.1 |
| 0.1 | | 400 | 40 | 2.85 |
| 0.2 | | 133 | 30 | — |
| 0.2 | | 400 | 45 | 7.3 |
| 0.3 | | 133 | 30 | 6.4 |
| 0.3 | | 400 | 45 | 16.8 |
| 0.1 | CsCl | 178 | 30 | — |
| 0.2 | | 178 | 33 | 6.4 |
| 0.3 | | 178 | 33 | 5.6 |
| 0.1 | LiCl | 235 | 30 | — |
| 0.1 | | 706 | 30 | 1.4 |
| 0.2 | | 235 | 30 | 1.4 |
| 0.2 | | 706 | 40 | 4.8 |
| 0.3 | | 706 | 45 | 10.2 |
| 0.1 | NH$_4$Cl | 190 | 30 | 0.6 |
| 0.1 | | 571 | 33 | 0.95 |
| 0.2 | | 190 | 37 | 2.3 |
| 0.2 | | 571 | 45 | 5.2 |
| 0.3 | | 190 | 30 | 10.7 |
| 0.3 | | 571 | 45 | 15.5 |
| 0.1 | MgCl$_2$ | 49 | 30 | 0.7 |
| 0.1 | | 148 | 30 | 1.7 |
| 0.2 | | 49 | 33 | 3.4 |
| 0.2 | | 148 | 33 | 5.7 |
| 0.3 | | 49 | 33 | 11.2 |
| 0.3 | | 148 | 45 | 13.9 |
| 0.3 | SrCl$_2$ | 31 | 33 | 4.6 |
| 0.3 | | 63 | 40 | 11.6 |
| 0.3 | | 188 | 45 | 10.6 |
| 0.05 | CaCl$_2$ | 202 | 33 | 0.5 |
| 0.1 | | 67 | 40 | 1.3 |
| 0.1 | | 202 | 45 | 3.5 |
| 0.2 | | 67 | 40 | 7.0 |
| 0.2 | | 202 | 45 | 8.0 |

TABLE-continued

| Properties of gel of the invention | | | |
|---|---|---|---|
| Polymer % w/v | Salt | Salt conc. (mM) | Melting temperature (°C.) | Gel strength (g · cm.$^{-2}$) |
| 0.3 | | 67 | 33 | 12.1 |
| 0.3 | | 335 | 40 | 13.9 |
| 0.3 | | 67 | 45 | 15.6 |
| 0.3 | | 202 | 45 | 16.6 |

In the Example hereinafter which illustrates the invention, reference is made to the accompanying drawings, in which.

(3a): Na$^+$ concentrations of 170 ( ■ ) and 500 ( ● ) nM ( 1% and 3% NaCl, respectively).

Figure 4:
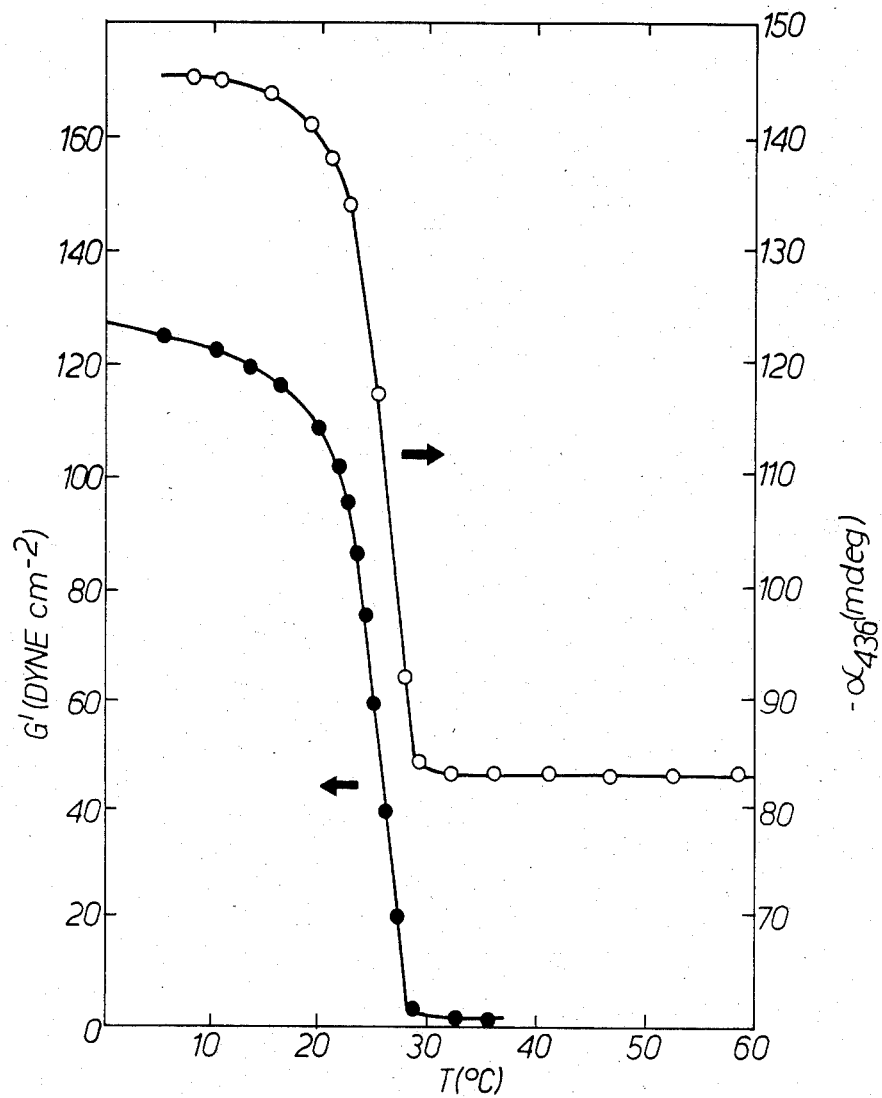
Figure 5:
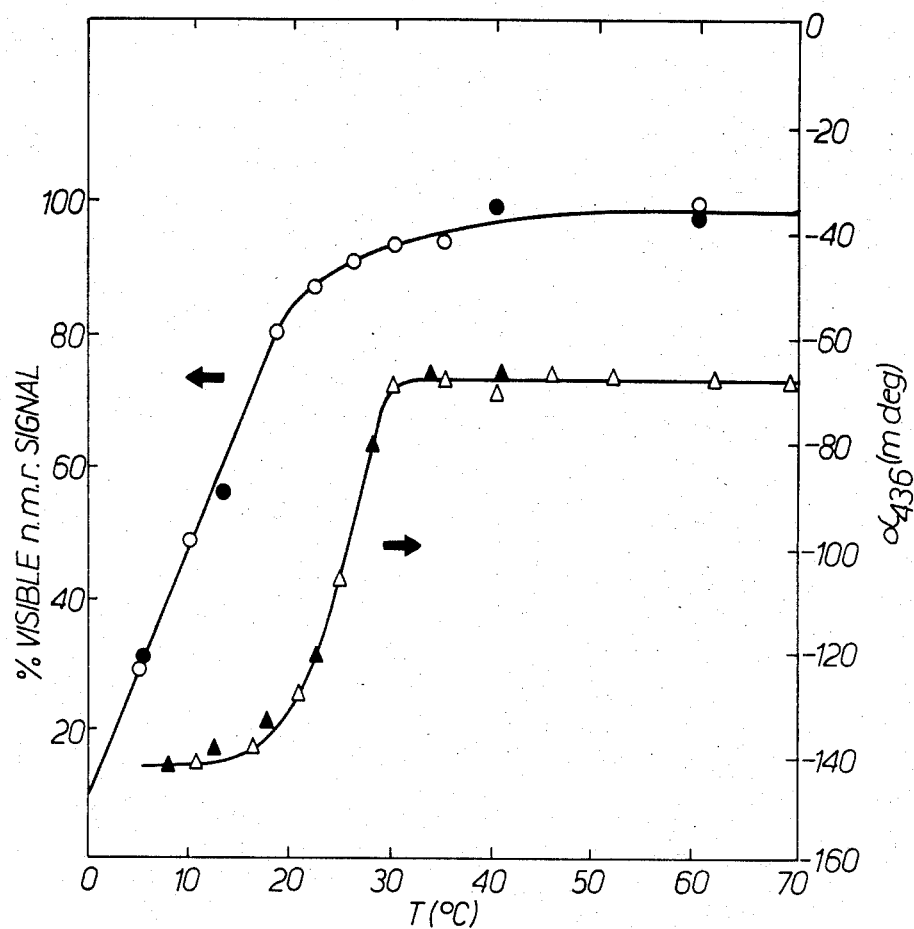
Figure 6:
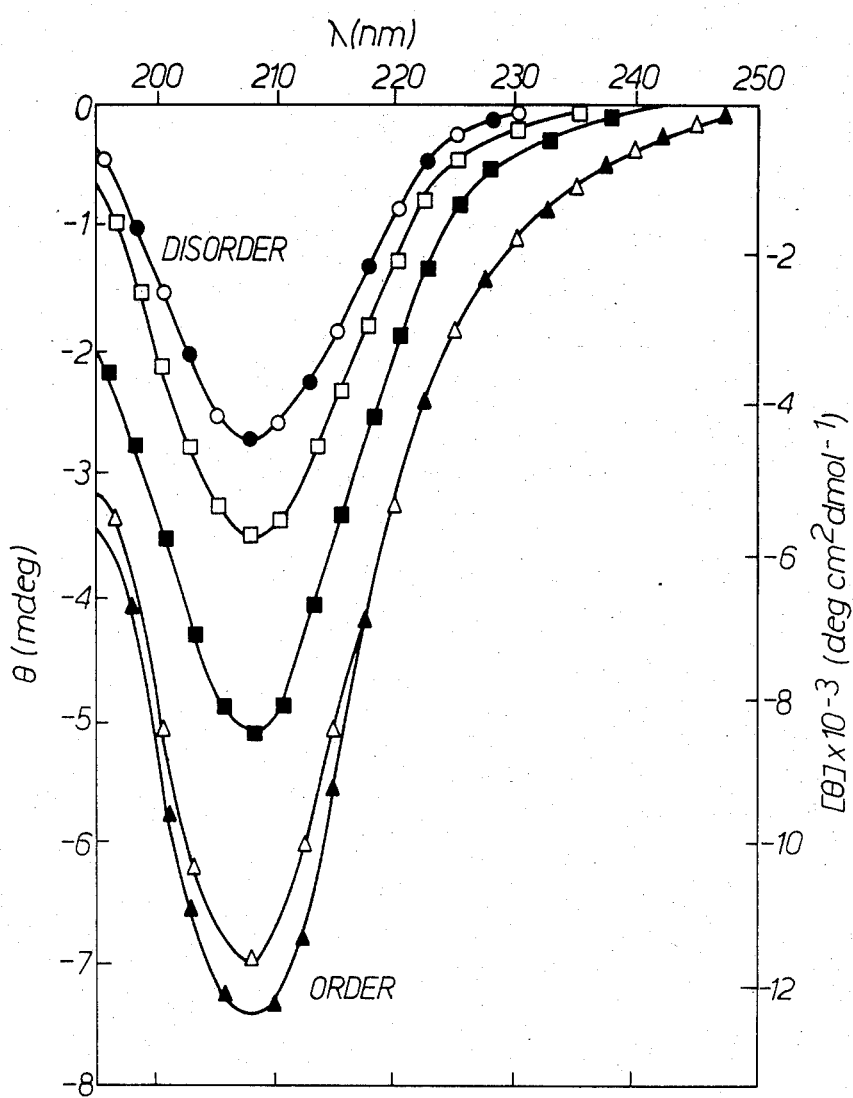

(3b): Ca$^{2+}$ concentrations of 67 ( ■ ) and 200 ( ● ) nM ( 1% and 3% CaCl$_2$.2H$_2$O, respectively);

FIG. 4 contains two graphs, in which the gel-sol transition (0.3 w/v; 0.2 M NaCl) is monitored by plotting the temperature against rigidity modulus G' ( ● ) and optical rotation (O), FIG. 5 contains two graphs in which the gel-sol transition of the polysaccharide (0.3 w/v in D$_2$O; 0.2 M NaCl) is monitored by loss of detectable high-resolution n.m.r. signal (circles) and by optical rotation (triangles); filled symbols show results obtained on heating and open symbols results obtained on cooling;

FIG. 6 is a plot of circular dichroism (theta) of the polysaccharide (0.3 w/v; 0.2 M NaCl) at 43 (o), 31 (●), 28 (□) 25 (■), 22 (△) and 13 (▲) °C. against wavelength.

Sugar ratios in the native and periodate-oxidised polymer were determined by alditol acetate analysis on a Pye 104 chromatograph, using columns of 3% SP-2340 on 100/120 Supelcoport, or OV 225. Uronic acid was determined by the method of N. Blumenkrantz and G. Asboe-Hansen, Anal. Biochem. 54, 184 (1973). Gels were prepared by addition of an appropriate salt solution to an aqueous solution to the polymer, heating to about 45° C. to melt the initial gel, and re-cooling. Solutions for optical studies were clarified by filtration through a 0.45 micrometer "Millipore" membrane.

Gel strength (yield stress) was determined using a simple penetrometer. Rigidity modulus was measured on a Rheometrics Mechanical Spectrometer (RMS-605) using the standard transducer with a 50 mm diameter cone and plate of cone angle 0.04 rad. Measurement was at 10 rad. s$^{-1}$ and 10% strain, using a heating rate of 1 degree/min for increasing the temperature of measurement. Solution viscosity measurements were made on a Ferranti cone and plate viscometer. Optical rotation was measured at 436 nm in a 10 cm pathlength cell on a Perkin Elmer 245 polarimeter, and circular dichroism spectra were recorded on a Jobin-Yvon Dichrograph Mk. V, using a 0.2 mm pathlength cell. In both cases, temperature was controlled by circulating water bath and monitored by a thermocouple within the cell, but out of the light path. High resolution proton n.m.r. measurements were made at 300 MHz on Bruker CXP 300 Fourier transform spectrometer. Peak areas were quantified relative to a standard pyrazine solution contained in a 2 mm-diameter capillary located centrally within the n.m.r. tube.

EXAMPLE

The bacterial strain NCIB 11870, as obtained in freeze-dried form, was plated out nutrient agar, MacConkey's agar or semi-synthetic medium containing glucose and yeast extracts. The polysaccharide was then prepared by culturing the bacterium on the same semi-synthetic medium using a 500 ml portion thereof shaken in a 2 liter Erlenmeyer flask. The polysaccharide was then recovered from the culture supernatant by precipitation with acetone or ethanol.

Hydrolysates of the polysaccharide (1 M trifluoroacetic acid at 100° C. for 16 hours) gave material chromatographically identical with glucose, fucose and glucuronic acid. Preparation of alditol acetates confirmed the identity of the neutral sugars and the colour development in the procedure of N. Blumenkrantz and G. Asboe-Hansen, supra, confirmed the presence of uronic acid. The molar ratio of sugar components L fucose: D-glucose: D-glucuronate of the polysaccharide was 1:3.3:1.06. After periodate oxidation the D-glucuronate was destroyed and the L-fucose: D-glucose molar ratio was 1:1.96. The D-configuration of the glucose residues was confirmed by glucose oxidase. No significant amounts of 0-acetyl groups or pyruvate ketal were detected.

Attempts to obtain oligosaccharides by partial acid hydrolysis were largely unsuccessful. However, autohydrolysis of a 0.5% (w/v) solution of the acid form of the polymer yielded one major oligosaccharide product. This proved to be an aldobiuronic acid, which on hydrolysis yielded equal quantities of fucose and glucuronic acid. Other oligosaccharides, obtained in smaller yield from the autohydrolysis were a trisaccharide containing approximately equimolar amounts of fucose, glucuronic acid and glucose and a tetrasaccharide in which the same three monosaccharides were present in the approximate molar ratio of 1:1:2. One neutral disaccharide containing D-glucose only was obtained.

Figure 1:
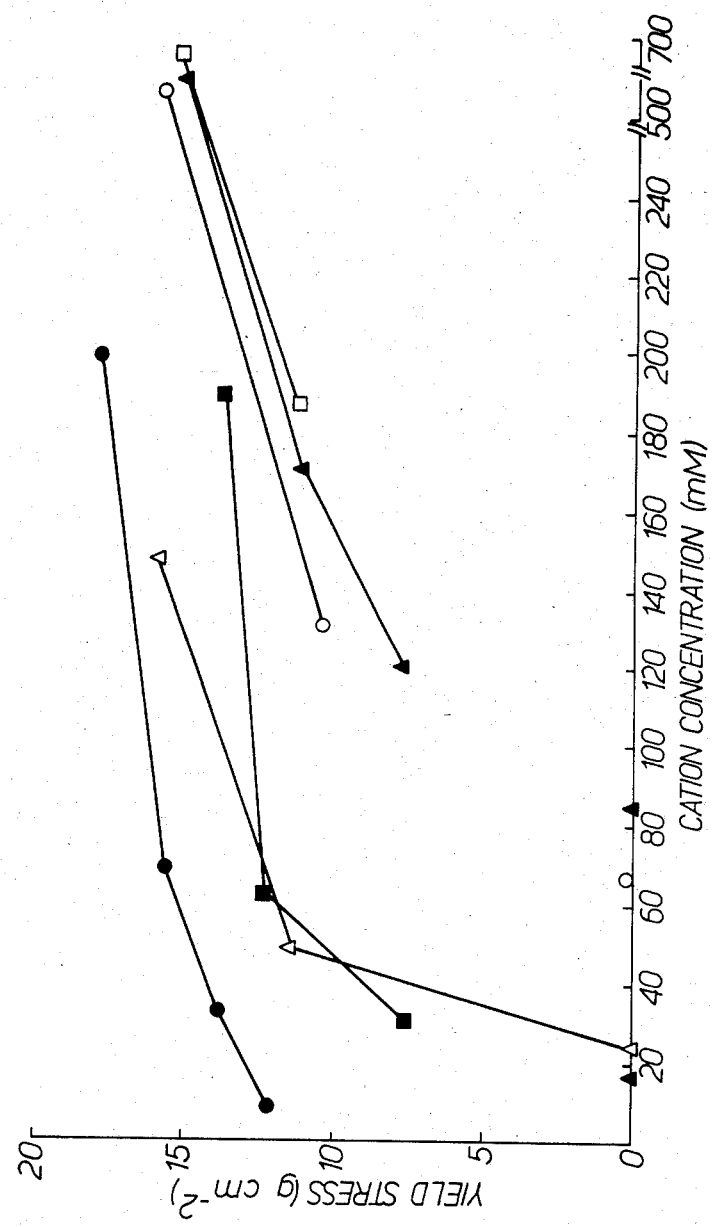
FIG. 1 is a graph showing the variation in gel strength (yield stress; 25° C.) of polysaccharide (0.3 w/v) with cation concentration, the cations shown (chloride salt form) being Na$^+$ ( ▲ ), K$^+$ (o), NH$_4^+$ ( □ ), Mg$^{2+}$ ( △ ), Ca$^{2+}$ ( ○ ) and Sr$^{2+}$ ( ● )

The strength (yield stress) of the gels of the invention formed at 0.3% w/v polymer concentration is shown in FIG. 1 for different concentrations of various cations (chloride salt form). In all cases, gel strength increases with increasing salt concentration.

Figure 2:
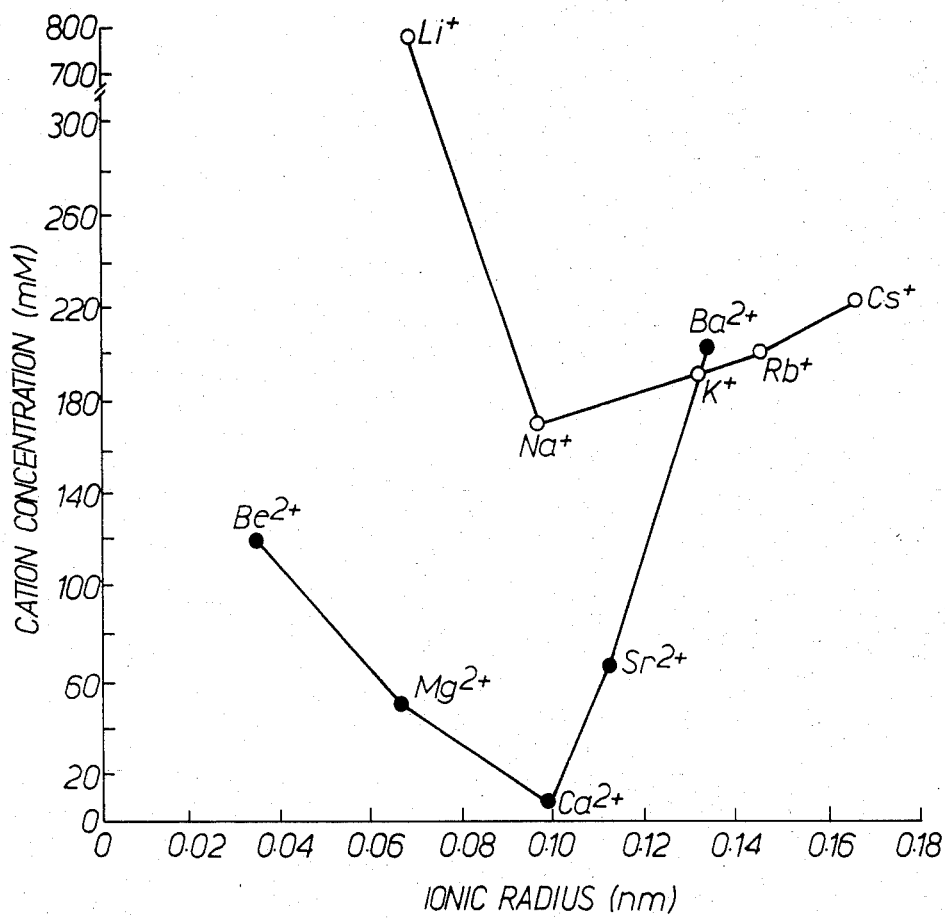
FIG. 2 is a graph showing molar concentrations of different cations (chloride salt form) required to produce gels (0.3 w/v polysaccharide; 25° C.) of the same strength (a yield stress of 10.9 g.cm$^{-2}$), the concentration being plotted against ionic radius.

There is considerable selectivity between different cations of the same valency. FIG. 2 shows the molar concentrations of Group Ia and Group IIa cations required to produce gels of the same strength, using a fixed concentration (0.3% w/v) of polymer. In both cases, optimum gelation is obtained at an ionic radius of about 0.1 nm (Na$^+$ and Ca$^{2+}$ respectively), with higher concentrations being required for both larger and smaller cations.

Figure 3A:
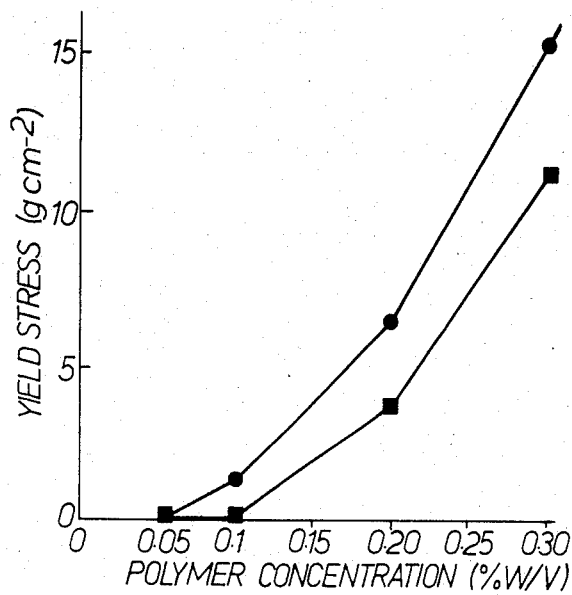
FIGS. 3a and 3b are graphs of polymer concentration against gel strength (yield stress; 25° C.), as follows.
Figure 3B:
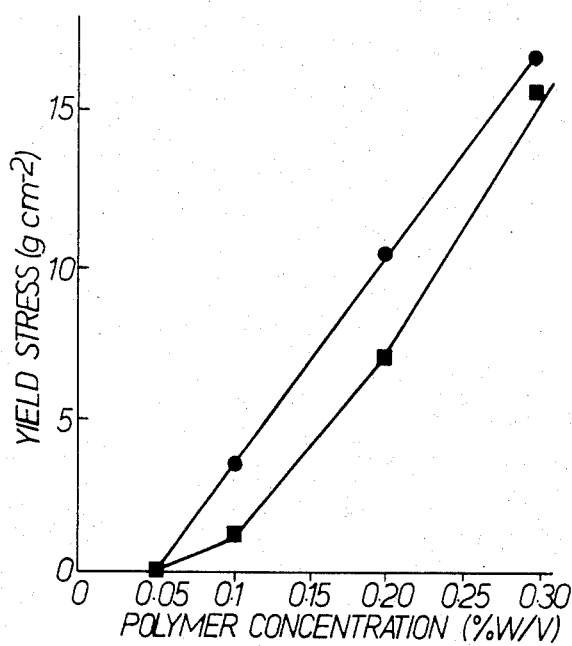

The minimum critical concentration of the polymer necessary for gelation also varies with the cation used (see Table above). For example, at the lower polysaccharide concentration tested (0.05% w/v) a gel was formed only with Ca$^{2+}$. At concentrations above the minimum required for gelation, gel strength increases with increasing polymer concentrations, as illustrated in FIG. 3.

The melting temperature of the polysaccharide gels shows little, if any, systematic variation with polymer concentration, but increases appreciably with increasing ionic strength (see Table above). Similar behaviour is well-known for other charged polysaccharides and can be attributed to suppression of electrostatic repulsion, thus facilitating interchain assoication and network formation.

The thermally-induced gel-sol transition of the polysaccharide is accompanied by a sharp change in optical rotation, with a closely similar temperature course (FIG. 4) to the loss of gel structure, as monitored by rigidity modulus (G'). Polysaccharide optical rotation is sensitive to chain geometry and an abrupt change of this type is indicative of a co-operative conformational transition, T. A. Bryce et al., Faraday Discuss. Chem. Soc. 57, 221 (1974). For example, the thermally-induced order-disorder transitions of agarose, S. Arnott, et al., J. Mol. Biol. 90, 269 (1974); carrageenan, A. A. McKinnon et al., Chem. Commun., 701 (1969); E. R. Morris et al., J. Mol. Biol. 138, 349 (1980) and xanthan, D. A. Rees, Biochem. J. 126, 257 (1972), G. Holzwarth Biochemistry 15, 4333 (1976); E. R. Morris et al., J. Mol. Biol. 110, 1 (1977); and M. Milas and M. Rinaudo, Carbohydr. Res. 76, 189 (1979); all give optical rotation-temperature profiles similar to that shown in FIG. 4. In comparison with these other polymers, however, the transition of the polysaccharide of the invention is usually sharp, suggesting a highly co-operative process between cation and polymer.

As shown in FIG. 5 the conformation transition indicated by optical rotation is accompanied by a progressive loss of detectable high resolution n.m.r. signal on cooling, as expected for adoption of a conformationally rigid, ordered strucrure. The changes in both optical rotation and n.m.r. are fully reversible (FIG. 5), with no detectable thermal hysteresis.

FIG. 6 shows the circular dichroism (c.d.) of the polysaccharide over a range of temperatures (13°-43° C.) spanning the sol-gel transition. The spectra are similar to those reported by E. R. Morris et al., J. Chem. Soc. Trans. Perkin II, 1418 (1975) for the carboxyl n→* transition of uronic acid glycosides, consistent with the presence of glucuronosyl residues in the primary structure of the polysaccharide. The negative sign of the observed c.d. band confirms the D configuration of these residues. Since neutral sugars such as glucose and fucose have no electronic transitions over the wavelength range shown in FIG. 6 and acetate and/or pyruvate substituents are present in negligible amounts, if at all, observed c.d. intensities may be expressed as molar ellipticity (theta) per glucuronate residue (FIG. 6 - right hand axis) using the polysaccharide composition data given hereinbefore.

The sol-gel transition of the polysaccharide is accompanied by an appreciable enhancement of c.d. intensity which follows the same temperature course as the change in optical rotation at higher wavelengths. The c.d. change between the sol and gel states is similar in form to the spectral changes observed on $Ca^{2+}$-induced gelation of alginate or pectate and centred at the same wavelength (about 208 nm), although of somewhat greater magnitude. The direction of c.d. change (to more negative values) for the D-glucuronate residues is the same as that for D-galacturonate in pectin, and opposite to that observed for L-guluronate residues of alginate (as expected for near mirror-image molecules experiencing the same perturbation). These close similarities in c.d. behaviour suggest that the underlying molecular process causing the c.d. change may also be similar in all three cases, i.e. specific site-binding of cations in close proximity to the carboxy chromophores.

The spectroscopic studies above indicate that gelation occurs by formation of extended, co-operative junction zones in which the participating chains are locked in a regular, ordered conformation, while on thermal melting the polymer reverts to the disordered ("random coil") state. The order-disorder transition is usually sharp, indicating a high degree of co-operativity. The absence of any detectable thermal hysteresis further suggests that interchain association is limited to the formation of ordered junctions involving a small, finite number of chains, rather than large aggregates as in the case of, for example, agarose.

The marked selectivity for cations of a particular ionic radius (FIG. 2) indicates specific incorporation of cations of the most appropriate size within the ordered structure, as in the "egg-box" binding of divalent cations in alginate and pectate gels, rather than non-specific "condensation" of ions along the polymer chain. The large, characteristic changes in carboxyl circular dichoism spectrum which accompany the sol-gel transition (FIG. 6) lend further support to this interpretation. These changes follow the same temperature course as the disorder-order transition the polymer chain (as measured by change in optical rotation), indicating that cation binding is an integral part of the ordering process, rather than occurring as a separate event.

I claim:

1. A polysaccharide having the following features:
   (1) it contains D-glucose, L-fucose and D-glucuronate residues in the approximate molar rtio of 3:1:1;
   (2) when oxidized by periodate it gives a product containing D-glucose residues of the unoxidized polymer, substantially all the L-fucose residues of the unoxidized polymer and substantially no D-glucuronate;
   (3) it forms gels when cations of at least any one of the elements lithium, sodium, potassium, rubidium and caesium opf Group Ia of the Periodic Table and magnesium, calcium, strontium and barium of Group IIa of the Periodic Table are added to an aqueous solution of the polymer;
   (4) the gels thus formed melt at a temperature effective to melt the gel but ineffective to decompose it and set on cooling reversibly;
   (5) the strength of the gels increases with increasing concentration of the polymer in aqueous solution;
   (6) the polymer forms stronger gels with Group Ia and IIa cations of an ionic radus of about 0.1 nm than with other Group Ia and IIa cations of smaller or larger ionic radius and
   (7) the polymer is obtainable by isolation from the bacterium NCIB 11870 or from a variant or mutant thereof.

2. A polysaccharide according to claim 1 wherein in item (6) of the definition the cations of Group Ia and IIa are sodium or calcium ions.

3. A polysaccharide according to claim 1 wherein the gel formed by addition of 0.17 M aqueous sodium chloride solution to a 0.3% w/v (g/100 ml) aqueous solution of the polymer at ambient temperature has a yield stress at 25° C. of at least 10 $g/cm^2$.

4. A gel comprising a polysaccharide defined in claim 1 and a gel-forming cation therefor.

5. A gel according to claim 4 wherein the ratio of cation to polymer is selected to impart to the gel the property of melting at a temperature in the range 30°–35° C.

6. A gellable aqueous composition containing a polysaccharide defined in claim 1 and a gel-forming cation.

7. A composition according to claim 6 wherein the ratio of cation to polymer is selected to impart to the gel the property of melting at a temperature in the range 30°–35° C.

* * * * *